United States Patent
Weber et al.

(10) Patent No.: US 10,620,216 B2
(45) Date of Patent: Apr. 14, 2020

(54) METHOD FOR DETERMINATION OF A PROTEIN

(71) Applicant: Bühlmann Laboratories AG, Schönenbuch (CH)

(72) Inventors: Jakob Weber, Pfeffingen (CH); Marie-Eve Überschlag, Bettlach (FR); Marianne Prica, Reinach (CH); Thomas Jermann, Röschenz (CH)

(73) Assignee: BUHLMANN LABORATORIES AG, Schonenbuch (CH)

( * ) Notice: Subject to any disclaimer, the term of this patent is extended or adjusted under 35 U.S.C. 154(b) by 70 days.

(21) Appl. No.: 15/312,097

(22) PCT Filed: May 20, 2015

(86) PCT No.: PCT/EP2015/061111
§ 371 (c)(1),
(2) Date: Nov. 17, 2016

(87) PCT Pub. No.: WO2015/177211
PCT Pub. Date: Nov. 26, 2015

(65) Prior Publication Data
US 2017/0108507 A1    Apr. 20, 2017

(30) Foreign Application Priority Data
May 21, 2014 (EP) .................... 14169355

(51) Int. Cl.
*G01N 33/53* (2006.01)
*G01N 33/68* (2006.01)
*G01N 33/543* (2006.01)

(52) U.S. Cl.
CPC ... *G01N 33/6827* (2013.01); *G01N 33/54393* (2013.01); *G01N 2333/4727* (2013.01)

(58) Field of Classification Search
CPC ......... G01N 33/6827; G01N 33/54393; G01N 2333/4727; G01N 33/53
See application file for complete search history.

(56) References Cited

U.S. PATENT DOCUMENTS 5,455,160 A   10/1995   Fagerhol et al.

FOREIGN PATENT DOCUMENTS

EP    0937259 B1    5/1998
WO    2011/146479 A1   11/2011

OTHER PUBLICATIONS

IDK Calprotectin ELISA (2014; retrieved from URL://search.cosmobio.co.jp/cosmo_search_p/search_gate2/docs/IMD_/K6927.20150721.pdf).*
Thermofisher ELISA (2006; retrieved from http://tools.thermofisher.com/content/sfs/brochures/1602127-Assay-Development-Handbook.pdf, whole publication).*
Kampanis et al., Ann Clin Biochem 2009; 46: 33-37, "Development and validation of an improved test for the measurement of human faecal elastase-1".
Whitehead, et al., Ann Clin Biochem 2013; 50: 53-61, "Between-assay variability of faecal calprotectin enzyme-linked immunosorbent assay kits".
Rodriguez-Otero, et al., Blood Journal.hematologylibrary.org on Jul. 21, 2014, vol. 119, No. 24, "Fecal calprotectin and alpha-1 antitrypsin predict severity and response to corticosteroids in gastrointestinal graft-versus-host disease".
Hege Ton, Clinica Chimica Acta 292 (2000) 41-54, Oct. 2, 1999, "Improved assay for fecal calprotectin".
DRG Calprotectin (MRP 8/14) Stool Elisa (EIA-5415), Mar. 4, 2014 (Vers. 5.1).
Heilmann, Journal of Veterinary Diagnostic Investigation, "Development and analytical validation of a radioimmunoassay for the measurement of alpha$_1$-proteinase inhibitor concentrations in feces from healthy puppies and adult dogs", May 1, 2011.
PhiCal Calprotectin ELISA Kit for the In Vitro Determination of Calprotectin (MRP 8/14, S100A8/A9/0 in Stool, Nov. 28, 2017.

* cited by examiner

*Primary Examiner* — Julie Wu
*Assistant Examiner* — Carmencita M Belei
(74) *Attorney, Agent, or Firm* — The Dobrusin Law Firm, P.C.

(57) ABSTRACT

The present invention concerns a method for determining the concentration of a protein in a gastrointestinal (GI) tract sample taken from a human or an animal. The present invention is characterized by the feature that a dilution of the sample in the buffered aqueous extraction medium in a range of 1:100 to 1:10,000 is obtained. The present invention leads to a significant improvement of the technical situation, and provides a simple, sensitive and specific determination tool of proteins in GI tract samples. The determination of proteins, e.g. calprotectin, elastases or hemoglobin, in GI tract samples leads to more accurate and reproducible results.

17 Claims, 4 Drawing Sheets

METHOD FOR DETERMINATION OF A PROTEIN

The present invention relates to a method for determination of a protein.

In particular, the present invention relates to a method for determining the concentration of a protein in a gastrointestinal (GI) tract sample taken from a human or an animal.

Many diseases show great influence on cellular metabolism. Several endogenously produced substances are released in a certain amount into the GI tract. Patients suffering from diseases like e.g. inflammatory diseases, allergic diseases, infectious diseases, food intolerance or cancer, release an increased or decreased amount of said endogenously produced substances into the GI tract. The presence or absence of said endogenously produced substances may be an important and valuable aspect for predicting and diagnosing a disease. Furthermore, any variations in the amount of said endogenously produced substances may be of great use in monitoring the progress of the disease. The efficacy of treatment and/or therapeutic procedures can additionally be evaluated and appropriate adjustments can be made.

One of above-mentioned substances released into the GI tract is calprotectin, a 36.5 kDa calcium binding protein consisting of three polypeptide chains. Calprotectin is also known as S100A8/A9, Calgranulin A/B, MIF-related Protein 8/14 (MRP8/14) or L1 protein and is abundant in neutrophil granulocytes, monocytes, macrophages, and submucosal epithelial cells. This protein exerts antimicrobial properties in vitro, both bactericidal and fungicidal. It also appears to have a regulatory function in inflammatory processes. Fecal calprotectin is therefore a marker of inflammatory diseases as well as of neoplastic diseases in the lower GI tract. Elevated concentrations of calprotectin in feces have been measured in patients with colorectal cancer, inflammatory bowel diseases and bacterial infections in the GI tract. The highest levels of calprotectin in plasma have been found in patients with rheumatoid arthritis, cystic fibrosis, Crohn's disease and acute bacterial infections such as sepsis and meningococcal disease. The determination of fecal calprotectin is therefore an important routine parameter for the monitoring of above-mentioned diseases, especially of inflammatory bowel diseases (Crohn's disease and ulcerative colitis) and colorectal cancer.

Human pancreas-elastase-1 is an anionic endoprotease with a molecular weight of 26 kDa. It belongs to the family of serine proteases and is a steroid-binding protein. This enzyme, in parallel to other digestive enzymes, is secreted from the pancreas into the duodenum. During intestinal passage pancreas-elastase-1 is bound to the bile salts and is not degraded. There is a linear correlation between elastase-1 secretion and lipase, amylase, and trypsin secretion of the pancreas. Furthermore, the elastase-1 secretion into the duodenum shows linear correlation to the concentration of elastase-1 in the stool. In human stool the concentration of pancreas-elastase-1 is five to six times higher than in the pancreas juice. These facts are important for diagnostic applications. Any disorders of the exocrine pancreas function are connected with reduced secretion of elastase-1 which results in a decreased concentration of the enzyme in the stool. Therefore, elastase-1 is used as a marker for the diagnosis of exocrine pancreatic insufficiency. It is also used for surveillance of the exocrine pancreatic function in diabetes mellitus, cystic fibrosis, and chronic pancreatitis.

Chymotrypsin is a proteolytic enzyme and a component of pancreatic juice acting in the duodenum where it performs proteolysis, the breakdown of proteins and polypeptides. It also belongs to the family of serine proteases. It is activated in the presence of trypsin.

Methods for the extraction and determination of a protein in a GI tract sample are well-known in the prior art.

In U.S. Pat. No. 5,455,160 a kit and a method for the determination of calprotectin in feces are disclosed which are presented as a diagnostic tool for use in the detection of cancer and inflammatory bowel diseases.

The publication of Tøn et al. (Clinica Chimica Acta 292 (2000) 41-54) is directed to an improved assay for fecal calprotectin. The authors describe a newly developed fecal sample preparation procedure for the measurement of calprotectin with higher calprotectin yield and lower contamination risk.

An important aspect of the method of Tøn et al. is that fecal calprotectin concentrations of samples diluted with 1:20 to 1:80 with buffer solution during sample extraction were increased to a higher degree as compared to the original sample dilution of 1:2 as described in U.S. Pat. No. 5,455,160.

Another very recent study by Whitehead et al. (Ann. Clin. Biochem. 50 (2013) 53-61) reported an up to 28% under-recovery of fecal calprotectin when using three different commercial extraction devices as compared to a manual weighing-in procedure. The recovery of one sample of watery consistency was only 5% to 45%. All samples were extracted by using a 1:50 dilution with the respective extraction buffer.

Starting from these disadvantages, the objective of the present invention is to improve the method for the determination of a protein.

This objective is solved by claim 1 of the present invention. Claim 1 concerns a method for determining the concentration of a protein in a gastrointestinal (GI) tract sample taken from a human or an animal, comprising the steps of
a) Collecting said sample and
b) Mixing the sample of step a) with a determined amount of a buffered aqueous extraction medium;
c) Homogenizing the mixture of step b) and
d) Performing an immunoassay by using the mixture obtained in step c);
e) Determining the concentration of the protein.

According to claim 1, the objective is solved by the feature that in step b) a dilution of the sample in the buffered aqueous extraction medium in a range of 1:100 to 1:10,000 is obtained.

Throughout the whole application the ratio of the dilution of the sample in the buffered aqueous extraction medium relates to the weight of the sample and to the volume of the buffered aqueous extraction medium, respectively, unless otherwise indicated.

This solution is contrary to the expectation of a person skilled in the art before the filing date of this application for the following reasons:

Tøn et al. tested several ratios between sample and buffered aqueous extraction medium (1:20, 1:50 and 1:80). Although they found a tendency towards an increased yield of the extracted protein with higher dilutions, there was no significant difference between the results. The correlation between the yields of calprotectin was strong, when the ratios were 1:20 and 1:50 between feces and extraction buffer, but there was a poor agreement between the two set of data meaning that the results were higher at a dilution of 1:50, however not significantly higher. When the ratios were 1:50 and 1:80 between feces and extraction buffer, the correlation between the two set of data was also strong, and there was a good agreement between the two set of data. Therefore Ten et al. concluded that increasing the dilution ratio beyond 1:50 did not affect the extraction yield significantly.

Surprisingly, it could be shown by the inventors that a dilution of the sample in the buffered aqueous extraction medium in a range of 1:100 to 1:10,000 during extraction leads to higher yields of proteins extracted from GI tract samples, preferably for samples containing a high protein concentration. A dilution of 1:50, as described in the prior art, is not sufficient to solve the above-mentioned objective.

Additionally the obtained results with dilutions in a range of 1:100 to 1:10,000 are more accurate as well as reliable and reproducible. This leads to a more accurate diagnosis of diseases. Furthermore, any variations of the protein concentrations in GI tract samples are detectable much easier which leads to a better monitoring of the progress of the disease. The efficacy of treatment and/or therapeutic procedures can be better evaluated and followed and appropriate adjustments can be made faster.

Furthermore, the inventors have surprisingly found that a mixture comprising the sample and the buffered aqueous extraction medium in a dilution in a range of 1:100 to 1:10,000 shows a much higher stability, i.e. the protein extracted from the GI tract sample into the buffered aqueous extraction medium, whereby a dilution in a range of 1:100 to 1:10,000 is obtained, is degraded much less or even not at all in a time period of at least one day up to 28 days at a temperature range of 2 to 42° C., preferably of 2 to 28° C., compared to a buffered aqueous extraction medium with a dilution of up to 1:80 as described in the prior art.

The method of the present invention is applied to a GI tract sample. The GI tract sample may be taken from any section of the GI tract. However, feces is preferred as it is easily available by non-invasive procedures.

The GI tract sample may be a watery or loose GI tract sample or a non-watery or solid GI tract sample.

An advantage of the method of the present invention is that it is also applicable to watery or loose GI tract samples.

In such samples the water content is variable and may be high, or even extremely high. Due to a dilution effect, the protein concentration in such watery GI tract samples may be lowered.

Nevertheless, the inventors have surprisingly found that the method of the present invention leads to accurate and reliable results in watery or loose GI tract samples in contrast to the methods of the prior art.

Furthermore, the method of the present invention is easily applicable even to such watery GI tract samples. In contrast, the methods available in the prior art used several complicated steps of drying the loose sample and then measuring the concentration of the protein in the dried feces.

The dry extraction method of Kampanis et al. (Ann. Clin. Biochem. 46 (2009) 33-37) may be mentioned with respect to the determination of elastase-1 in human feces. The described method is disadvantageous as it takes longer to prepare samples when compared with the conventional wet extraction method (e.g. with the ScheBo Biotech E1 Quick-Prep™ tube; dilution ratio 1:70). Therefore in practice, its use has been limited to loose and wet samples. The wet or loose feces samples have to be dried, then weighed and finally accordingly diluted with extraction solution. This is very labor-intensive and not very hygienic. Another disadvantage with this approach is the difference in reference concentrations between the two extraction methods, as there is a risk that users will apply the wrong one. This in turn may lead to false diagnoses or incorrect therapy decisions.

As the method of the present invention leads to accurate and reliable results, further unnecessary investigations, inappropriate use of resources and patient management are avoided. Despite very high water content such samples are suitable for analysis, therefore any delay of biochemical diagnosis and initiation of appropriate treatment is avoided.

The GI tract sample may come from a human or an animal, preferably a human. The animal may preferably be a dog, cat, monkey, bovine, pig, horse, rat or mouse as these animals can develop similar symptoms as humans which can be followed by increased amounts of mentioned fecal proteins.

The GI tract sample may be collected during invasive methods, e.g. operations and biopsies, or from excrements.

In the method of the present invention, the collecting according to step a) may be carried out using a special, quantitative dosing tip, an inoculation loop, a small spoon, a syringe or a pipette (tip). This has the advantage that disposable tools may be used, so the health risk to laboratory personnel is comparably small. Additionally there is almost no environmental and operator contamination. Furthermore, the risk of cross-contamination of samples is extremely low.

In case the GI tract sample is a non-watery GI tract sample, step a) may be carried out by introducing the collecting tool into different locations of the sample. The advantage of such sampling is that any local differences in protein concentration are eliminated.

In case the GI tract sample is a watery GI tract sample, step a) may preferably be carried out using a quantitative syringe or by quantitative pipetting.

The amount of sample which is collected in step a) of the method of the present invention is preferably in a range of 1 to 1,000 mg, more preferably in a range of 2 to 100 mg, even more preferably in a range of 4 to 20 mg, and most preferably in a range of 8 to 12 mg in case the GI tract sample is a non-watery GI tract sample.

The amount of sample which is collected in step a) of the method of the present invention is preferably in a range of 1 to 1,000 µl, more preferably in a range of 2 to 100 µl, even more preferably in a range of 4 to 20 µl, and most preferably in a range of 8 to 12 µl in case the GI tract sample is a watery GI tract sample.

The use of such small sample sizes of feces has the advantage that it is easy to obtain from any patients, even from children, elderly or frail subjects. Such a small amount of feces may easily be stored, even if the samples require freezing.

In step b) of the method of the present invention the sample of step a) is mixed, preferably directly mixed, with a determined amount of a buffered aqueous extraction medium. The term "directly" in this context means that no further processing steps are carried out with the sample between steps a) and b), e.g. pre-dilution, drying, extraction, washing or heat-treatment.

The buffer substance of the buffered aqueous extraction medium may be selected from phosphate, maleate, chloroacetate, formate, benzoate, pyridine, piperazine, propionate, 3-N-morpholinopropanesulfonic acid (MOPS), 1,3-bis(tris(hydroxymethyl)methylaminopropane (Bis-TRIS), tris-(hydroxymethyl)aminomethane (TRIS), tris-(hydroxymethyl)aminomethane-maleic acid (TRIS-maleate), 2-(tris(hydroxymethyl)methylamino)ethanesulfonic acid (TES), 1,4-piperazine-bisethanesulfonic acid) (PIPES), 4-morpholinoethanesulfonic acid (MES), N-2-hydroxyethylpiperazine-N'-2-ethanesulfonic acid (HEPES), N,N-bis(2- hydroxyethyl)-2-aminoethanesulfonic acid (BES), N-(2-acetamido)iminodiacetic acid (ADA), N-(2-acetamido)-2-aminoethanesulfonic acid (ACES), and others known to a person skilled in the art. Any mixtures of said buffer substances may also be employed in step b) of the method of the present invention. The buffered aqueous extraction medium may contain salts, antimicrobial agents, detergents, chelating agents, chaotropic agents, and/or anti-foaming agents. In principle any buffered aqueous extraction media may work properly for the present invention.

The amount of buffered aqueous extraction medium may be chosen so as to obtain a dilution of the sample in the buffered aqueous extraction medium in a range of 1:100 to 1:10,000. Preferably the dilution is in a range of 1:100 to 1:2,000, more preferably the dilution is in a range of 1:200 to 1:1,000, still more preferably the dilution is in a range of 1:450 and 1:550, and most preferably the dilution is 1:500. The dilution of the sample in the buffered aqueous extraction medium in a range of 1:100 to 1:10,000 is preferably obtained in one step.

The concentration of the buffer substance in the buffered aqueous extraction medium may be chosen from a concentration of 0.1 mM to 2 M, preferably of 10 mM to 0.2 M, and most preferably of 20 to 50 mM.

Further the pH for the mixing according to step b) of the method of the present invention depends on the buffered aqueous extraction medium which may be used in step b) and may be chosen in a range of pH 3 to pH 12, preferably in a range of pH 5 to pH 9, and most preferred at pH 7.5.

The mixing according to step b) of the method of the present invention may be carried out at a temperature range of 2° C. to 45° C., preferably of 10° C. to 35° C., more preferred of 18° C. to 28° C., and most preferred at a temperature of 23° C.

The homogenizing according to step c) of the method of the present invention may preferably be carried out in a closed vessel.

The homogenizing according to step c) of the method of the present invention may be carried out by manual shaking, by using a vortex mixer or an end-over-end mixer (rotary mixer), or by applying shearing forces by using a syringe and pipette, respectively, or by applying ultrasound.

In case the homogenizing according to step c) is carried out by manual shaking, by applying shearing forces by using a syringe and pipette, respectively, or by applying ultrasound, the period may be at least 5 seconds, preferably in a range of 5 to 600 seconds, more preferably in a range of 10 to 60 seconds.

In case the homogenizing according to step c) is carried out by using a vortex mixer, the period may be at least 5 seconds, preferably in a range of 5 to 300 seconds, more preferably in a range of 10 to 60 seconds. The speed of the vortex mixer may be chosen from a range of 100 to 10,000 rpm, preferably the speed may be the maximum available.

In case the homogenizing according to step c) is carried out by using an end-over-end mixer (rotary mixer), the period may be at least 5 minutes, preferably in a range of 5 minutes to 24 hours, more preferably in a range of 10 to 180 minutes, still more preferably in a range of 15 to 60 minutes. The speed of the rotary mixer may be chosen from a range of 10 to 1,000 rpm, preferably the speed may be the maximum available.

The homogenizing step c) may include a period of time during which the mixture is allowed to stand. Additionally, this may lead to sedimentation of solid components still present in the mixture. Preferably the time is chosen from a range of 5 minutes to 24 hours, more preferably from a range of 10 to 60 minutes.

The homogenizing step c) may be repeated several times, preferably twice, in order to remove the complete non-watery GI tract sample material from the collecting tool, e.g. the dosing tip of the sampling pin.

It is preferred, that the homogenizing step c) is directly performed, and no further processing steps are carried out with the mixture of step b).

Furthermore, it is preferred, that the complete extraction process (i.e. steps b) and c) according to the method of the present invention) is carried out at a dilution in a range of 1:100 to 1:10,000. In the methods according to the state of the art first the extraction takes place at a dilution of the sample in the buffered aqueous extraction medium of up to 1:80, and then further dilutions are carried out after the homogenizing step.

In step d) of the method of the present invention the mixture obtained in step c) is used, preferably directly used, and an immunoassay is performed. The term "directly" in this context means that no further processing steps are carried out with the mixture of step c) between steps c) and d), e.g. centrifugation, extraction, further homogenization, or filtration. This is advantageous as it is less time and resource consuming than the methods known in the prior art. In the prior art methods a person skilled in the art has to apply a centrifugation step to the homogenized sample. The supernatant has to be separated, further diluted with assay buffer, and is then used for further analysis.

The immunoassay performed in step d) depends on the protein to be determined in the GI tract sample.

The protein may be selected from the group comprising lactoferrin, elastases (such as PMN-elastase, elastase-1, elastase-2A, elastase-2B, elastase-3A, elastase-3B), M2-pyruvate kinase, hemoglobin, haptoglobin, hemoglobin/haptoglobin complex, chymotrypsin, lysozyme, albumin, pre-albumin, beta-defensin 2, alpha-1-antitrypsin, alpha-2-macroglobulin, carbonic anhydrase I, carbonic anhydrase II, myeloperoxidase, eosinophil-derived neurotoxin, eosinophilic peroxidase, major basic protein-1, Charcot Leiden Crystal protein (CLC/GAL10), eosinophilic protein X, C-reactive protein, immunoglobulins, secretory IgA, anti-tissue transglutaminase antibodies, anti-gliadin antibodies, anti-deamidated gliadin antibodies, interleukins (such as interleukin-1, interleukin-6, interleukin-8), tumor necrosis factor-alpha, antigens of pathogens, antibodies to pathogens, anti-*H. pylori* antibodies, S100 proteins, calgranulin C (S100A12; EN-RAGE), calgranulin B (S100A8; MIF-related protein 8), calgranulin C (S100A9; MIF-related protein 14), and calprotectin (calgranulin A/B; S100A8/A9; MIF-related protein 8/14).

However calprotectin, an elastase or hemoglobin is particularly preferred.

Fecal calprotectin is a marker of inflammatory as well as of neoplastic diseases in the GI tract. Elevated concentrations of calprotectin in feces have been measured in patients with colorectal cancer, inflammatory bowel diseases (Crohn's disease and ulcerative colitis), appendicitis and bacterial infections in the GI tract. Fecal calprotectin is also used to differentiate between inflammatory bowel disease (IBD; usually high concentrations of calprotectin) and irritable bowel syndrome (IBS; usually low or absent levels of calprotectin).

Reduced concentrations of elastases are used as markers for the diagnosis of exocrine pancreatic insufficiency. It is also used for the surveillance of the exocrine pancreatic function in diabetes mellitus, cystic fibrosis, and chronic pancreatitis.

Elevated levels of fecal hemoglobin (so-called fecal occult blood) are associated with colorectal cancer. Therefore, this marker is widely used for colorectal cancer screening.

The accurate determination of fecal proteins is therefore mandatory for the correct diagnosis and accurate monitoring of above-mentioned diseases, especially of inflammatory bowel diseases (Crohn's disease and ulcerative colitis) and colorectal cancer.

In the prior art immunoassays for the determination of above-mentioned proteins are available. A person skilled in the art does know which assay to choose.

Preferably, the immunoassay is selected from the group comprising an enzyme-linked immunosorbent assay (ELISA), an immunoturbidimetric assay, an immunochromatographic (lateral flow) assay and a flow-assisted cytometric assay.

In step e) of the method of the present invention the concentration of the protein is determined.

The determination of the concentration in step e) of the method of the present invention is carried out by a method selected from the group comprising reflectometry, absorbance, fluorescence, chemiluminescence, electrochemiluminescence, UV/VIS spectroscopy, amperometry, magnetometry, voltametry, potentiometry, conductometry, coulometry, polarography, and electrogravimetry.

In an alternative embodiment the determination in step e) of the method of the present invention is carried out visually. Such a determination is easy and may be carried out without further equipment.

In case of a non-watery GI tract sample, the concentration of the protein is in a range of 1 ng/g of the sample to 100 mg/g of the sample, preferably in a range of 10 µg/g of the sample to 10 mg/g of the sample.

In case of a watery GI tract sample, the concentration of the protein is in a range of 1 ng/ml of the sample to 100 mg/ml of the sample, preferably in a range of 10 µg/ml of the sample to 10 mg/ml of the sample.

In a preferred embodiment the protein concentration in the sample is higher than 300 µg/g of the sample in case of a non-watery GI tract sample and 300 µg/ml of the sample in case of a watery GI tract sample. The inventors have surprisingly found that with such high amounts of protein the method of the present invention provides more accurate and reliable results than the methods of the prior art.

The protein exhibits generally an excellent stability when present in the GI tract sample matrix (e.g. feces; see Tøn et al., Clinica Chimica Acta 292 (2000) 41-54). But when the protein is extracted with a buffered aqueous extraction medium out of the GI tract sample matrix (e.g. feces) into a solution or suspension, the protein may show a reduced stability depending on storage conditions such as constitution of the buffered aqueous extraction medium, storage temperature, storage time, etc. Sample extract (=extracted protein) stability is particularly critical if the feces sample is collected at a different place (e.g. at patient's home) into a container prefilled with buffered aqueous extraction medium and then sent to the testing laboratory, particularly when the shipping takes several days at ambient temperature.

The criterion of stability is connected to the amount of degradation of a protein.

The degradation of a protein, e.g. calprotectin, is defined in this context of the present invention by the recovery of said protein in the mixture obtained in step c). The recovery may be calculated by the following equation:

$$\text{Recovery} = [(\text{Concentration of extracted protein at } t_1 \text{ at } T_1)/(\text{Concentration of extracted protein at } t_0 \text{ at } T_0)] \times 100\%.$$

The concentration of the extracted protein in solution or suspension may be determined according to methods known in the prior art or with the methods of the present invention (see Examples 1 and 2 below).

First, the concentration of said protein is determined at time 0 ($t_0$) at a temperature $T_0$, i.e. the fecal extract is measured immediately after the respective extraction according to the inventive method. The term "immediately" means that the determination of the concentration is carried out in a time period of 5 to 120 minutes after steps b) and c) of the method of the present invention. Preferably the temperature $T_0$ is ambient temperature, i.e. 20 to 25° C.

The fecal extract is then incubated for a pre-defined time $t_1$ at a pre-defined temperature $T_1$ (e.g. one day at 28° C.). After said time $t_1$ the concentration of said protein is determined again.

Surprisingly, it has been found by the inventors that the proteins were much more stable, particularly at elevated temperatures, when extracted from the GI tract sample with a buffered aqueous extraction medium using an extractive dilution in a range of 1:100 to 1:10,000, as compared to an extractive dilution of 1:50, and stored afterwards at a pre-defined temperature for a pre-defined time.

In a preferred embodiment the protein in the buffered aqueous extraction medium is stable in a temperature range of 2 to 42° C., more preferably of 2 to 28° C., for a time period of 1 to 28 days, when an extractive dilution in a range of 1:100 to 1:10,000, preferably of 1:500, is used as compared to an extractive dilution of 1:50.

Calprotectin e.g. was perfectly stable when extracted from GI tract samples with a buffered aqueous extraction medium using a dilution factor of 1:500, at a temperature in a range of 2 to 8° C. as well as at 28° C. for up to 6 days. No degradation was visible at an extractive dilution of 1:500, i.e. the recovery was equal to or greater than 100% (see Example 10).

A stability coefficient, SC, may be calculated by the following equation:

$$SC = (\text{Recovery of extracted protein at } t_1 \text{ at } T_1 \text{ in dilution } 1{:}X)/(\text{Recovery of extracted protein at } t_1 \text{ at } T_1 \text{ in dilution } 1{:}50)$$

whereby X is a value in the range of 100 to 10,000 and $t_1$ and $T_1$ are as defined above.

The stability coefficient may be at least 1.001, preferably in a range of 1.001 to 15, preferably in a range of 1.001 to 8, more preferably in a range of 1.001 to 5, still more preferably in a range of 1.001 to 2, and most preferably in a range of 1.001 to 1.7.

Figure 1:
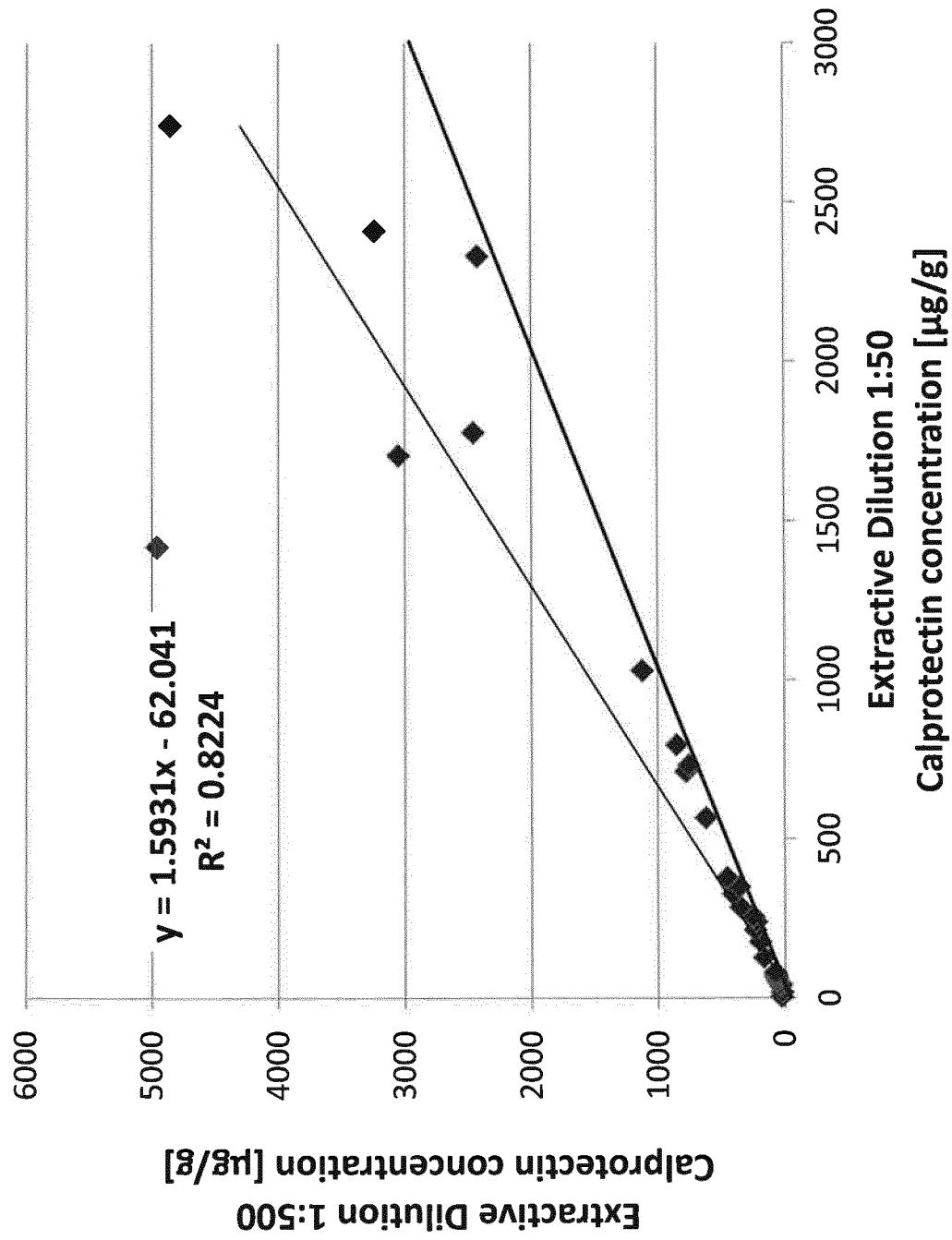
FIG. 1.

Comparison of 33 feces samples extracted with a dilution factor of 1:50 versus a dilution factor of 1:500. The thin line represents the regression line between the matching sample pairs (slope: y=1.5931x). The bold line represents the hypothetical identity line between the matching sample pairs (slope: y=1.00x).

FIG. 2:

Comparison of 29 feces samples with calprotectin concentrations above 300 µg/g of the sample extracted with a dilution factor of 1:50 versus a dilution factor of 1:500. The fecal samples are sorted by increasing concentrations measured with the 1:50 extractive dilution. The speckled bars represent the calprotectin concentrations determined with an extractive dilution of 1:50. The solid bars represent the calprotectin concentrations determined with an extractive dilution of 1:500. Samples measuring higher than 6,000 µg/g of the sample were not further diluted in the ELISA assay and are shown as "6000 µg/g".

FIG. 3:

Six feces samples with calprotectin concentrations in a range of 50 to 1,800 µg/g of the sample were extracted using dilution factors of 1:50 and 1:500, respectively, with 3 different commercial extraction buffers and analyzed in two different commercial ELISA tests. All data points measured for the two different extractive dilutions were summarized, and the matching data pairs were compared by regression analysis. The solid, bold line represents the hypothetical identity line between the matching sample pairs (slope: y=1.00x), whereas the dashed line represents the true regression line through all 30 matching data pairs (slope: y=2.8612x).

FIG. 4:

40 feces samples with calprotectin concentrations in a range of 20 to 2,500 µg/g of the sample were extracted with a dilution factor of 1:500 using two different extraction methods (the BÜHLMANN Calex™ Cap device by pipetting-in and a manual weighing-in procedure, respectively) and analyzed in the BÜHLMANN Calprotectin ELISA. The matching data pairs were compared by regression analysis. The fine line represents the hypothetical identity line between the matching sample pairs (slope: y=1.00x), whereas the solid, bold line represents the true regression line through all 40 matching data pairs (slope: y=0.9636x).

The characteristic effects and advantages of the present invention are illustrated by the following non-limiting examples.

EXAMPLE 1: EXTRACTION OF FECES SAMPLES

Feces were obtained from anonymized surplus stool samples kindly provided by local routine laboratories and the gastroenterology department of the University Hospital of Basel. Upon receipt, samples were either stored at 2 to 8° C. for up to one week or at <−20° C. for longer periods of time (up to two years). The feces samples were equilibrated to ambient temperature (20 to 25° C.) prior to extraction and were then extracted as follows:

a) "Reference Method": 60 to 100 mg of feces were weighed into the sample chamber of the Smart-Prep device (B-CAL-RD, BÜHLMANN Laboratories AG, Schoenenbuch, Switzerland) by using either a small spoon for non-watery samples or a quantitative pipette for watery (liquid) samples. In the latter case, 60 to 100 µl of watery feces was pipetted into the sample chamber as the density of an average feces sample is close to 1 g/ml. Accordingly, 3 to 5 ml of extraction buffer (B-CAL-EX, BÜHLMANN Laboratories AG, Schoenenbuch, Switzerland) were added resulting in an extraction factor of 1:50. The Smart-Prep device was then vortexed at maximum speed for 1 minute and the resulting homogenate was allowed to sediment for 30 minutes. Aliquots of the supernatant were then used for the respective Calprotectin ELISA assay (see Example 2).

b) In order to generate alternative extraction factors of feces vs. extraction buffer of 1:100, 1:250, and 1:500, approximately 40 mg (40 µl), 30 mg (30 µl), and 15 mg (15 µl) of feces were weighed (pipetted) into the sample chamber of the Smart-Prep device (B-CAL-RD, BÜHLMANN Laboratories AG, Schoenenbuch, Switzerland), respectively. Accordingly, approximately 4 ml, 7.5 ml, and 7.5 ml of extraction buffer (B-CAL-EX, BÜHLMANN Laboratories AG, Schoenenbuch, Switzerland), respectively, were added to obtain the respective extractive dilution factors. Extractive dilution factors of 1:1,000 and 1:5,000 were obtained by weighing (pipetting) of 20 mg (20 µl) and 10 mg (10 µl) of feces into 50 ml-Falcon Tubes (ThermoFisher Scientific AG, Reinach, Switzerland), and adding 20 ml and 50 ml of extraction buffer (B-CAL-EX, BÜHLMANN Laboratories AG, Schoenenbuch, Switzerland), respectively. All filled devices were then vortexed at maximum speed for 1 minute and the resulting homogenates were allowed to sediment for 30 minutes. Aliquots of the supernatants were then used for the respective Calprotectin ELISA assay (see Example 2).

c) Alternatively, the CALEX™ Cap and CALEX™ Valve devices (BÜHLMANN Laboratories AG, Schoenenbuch, Switzerland), respectively, were used to obtain an extraction factor of 1:500. The devices consist of a sampling pin, an extraction chamber of approximately 8 ml of volume and either a closing screw cap (CALEX™ Cap) or a valve portion (CALEX™ Valve) at the other end to transfer the resulting feces extract to the analyzing devices. The sampling pin with 8 to 10 grooves (total volume of the grooves corresponds to the volume of 10 mg of feces) was introduced three to five times into a non-watery feces sample in order to completely fill the grooves. Then the sampling pin was introduced through a funnel located at the opening of the extraction chamber whereby excess feces is stripped off and exactly 10 mg of feces is transferred into the extraction chamber, which was previously filled with 5 ml of extraction buffer (B-CAL-EX, BÜHLMANN Laboratories AG, Schoenenbuch, Switzerland), thereby generating an extraction factor of 1:500. In case of watery (liquid) feces samples 10 µl of feces were introduced by a precision pipette through the funnel located at the opening of the extraction chamber and the device was closed by pushing the sampling pin into its closed position. The devices were then manually and vigorously shaken for at least twice 10 seconds or until all remaining feces was removed from the grooves of the sampling pin or were vortexed for 30 to 60 seconds at maximum speed. The resulting homogenates were allowed to sediment for 30 minutes. Aliquots of the supernatants and/or the homogenates were then used for the respective Calprotectin assays (see Example 2).

EXAMPLE 2: CALPROTECTIN ASSAYS

If not mentioned explicitly, the BÜHLMANN Calprotectin sandwich ELISA (EK-CAL; BÜHLMANN Laboratories AG, Schoenenbuch, Switzerland) was used to assess the concentrations of calprotectin in extracted fecal samples. The fecal extracts obtained in Examples 3 to 10 were further diluted with incubation buffer (B-CAL-IB; BÜHLMANN Laboratories AG, Schoenenbuch, Switzerland) in a range of 1:5 to 1:150 and 100 µl of the diluted fecal sample extract as well as 100 µl of prediluted calibrators and controls were pipetted in duplicates into wells of a microtiter plate coated with a highly specific anti-calprotectin antibody (B-CAL-MP; BÜHLMANN Laboratories AG, Schoenenbuch, Switzerland). Subsequently, 100 μl of a second monoclonal anti-calprotectin antibody conjugated to horse-radish peroxidase (enzyme label B-CAL-EL; BÜHLMANN Laboratories AG, Schoenenbuch, Switzerland) was added to each well and the microtiter plate was then incubated on a rotatory shaker (400-600 rpm) for 30 minutes at ambient temperature (18-28° C.). After extended washing 100 μl of a TMB substrate solution (B-TMB12; BÜHLMANN Laboratories AG, Schoenenbuch, Switzerland) was added to each well and the microtiter plate was incubated on a rotatory shaker (400-600 rpm) for 15 minutes at ambient temperature (18-28° C.). After adding 100 μl of a stopping solution the absorbance of each well was measured at 450 nm in the SpectraMax® 190 microtiter plate reader (Molecular Devices, Sunnyvale, Calif., USA). The absorbance of the calibrators (on the vertical axis) was plotted vs. their respective calprotectin concentrations (on the horizontal axis), and the best fitting standard curve was drawn using a 4-parameter logistics fit. The absorbance of controls and extracted fecal samples were then intersected with the standard curve and the resulting calprotectin concentrations were read from the horizontal axis. Finally, the read calprotectin concentrations were corrected for the different dilution factors where necessary. Alternative calprotectin ELISAs were used accordingly.

EXAMPLE 3: EFFECT OF DILUTION FACTOR 1:50 VS. 1:500 DURING EXTRACTION PROCESS ON CALPROTECTIN YIELD 33 feces samples were extracted either according to Example 1a) (extractive dilution 1:50) or according to Example 1b) (extractive dilution 1:500) and assayed in the BÜHLMANN Calprotectin ELISA as described in Example 2. The results are listed in Table 1 and are graphically illustrated in FIG. 1. It can clearly be seen that samples showing a calprotectin concentration above approximately 300 μg/g of the sample are measuring higher at an extractive dilution of 1:500 as compared with 1:50, in particular feces samples above 1,000 μg/g of the sample.

TABLE 1

| Feces Sample | Calprotectin Conc. [μg/g of the sample] 1:50 | Calprotectin Conc. [μg/g of the sample] 1:500 |
|---|---|---|
| 16 | 3 | 30 |
| 9 | 18 | 25 |
| 15 | 36 | 38 |
| 6 | 39 | 38 |
| 13 | 43 | 36 |
| 12 | 43 | 47 |
| 27 | 51 | 60 |
| 2 | 59 | 64 |
| 14 | 64 | 70 |
| 31 | 65 | 77 |
| 21 | 71 | 69 |
| 8 | 73 | 78 |
| 25 | 80 | 78 |
| 4 | 125 | 167 |
| 11 | 175 | 196 |
| 10 | 213 | 237 |
| 5 | 238 | 230 |
| 22 | 253 | 249 |
| 20 | 283 | 351 |
| 28 | 326 | 411 |
| 3 | 348 | 363 |
| 18 | 376 | 457 |
| 30 | 565 | 623 |
| 26 | 711 | 781 |

TABLE 1-continued

| Feces Sample | Calprotectin Conc. [μg/g of the sample] 1:50 | Calprotectin Conc. [μg/g of the sample] 1:500 |
|---|---|---|
| 39 | 731 | 756 |
| 17 | 795 | 853 |
| 32 | 1,028 | 1,125 |
| 35 | 1,417 | 4,961 |
| 38 | 1,704 | 3,053 |
| 37 | 1,776 | 2,462 |
| 19 | 2,329 | 2,428 |
| 29 | 2,409 | 3,244 |
| 33 | 2,739 | 4,857 |

Figure 2:
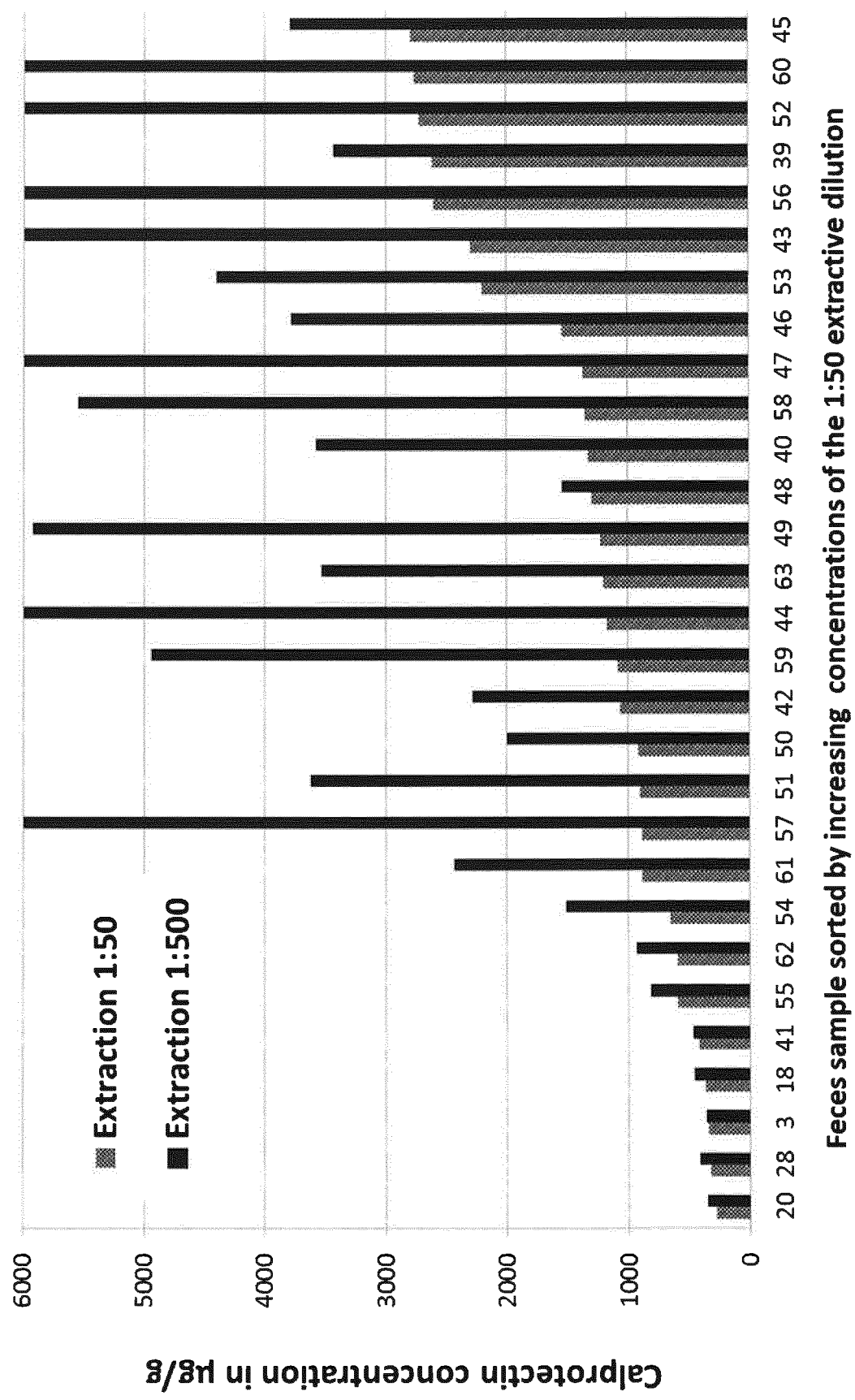

Subsequently, 29 additional samples with calprotectin concentrations higher than 300 μg/g of the sample were tested in the same way as described above. The results are shown in Table 2 and FIG. 2. All samples examined exhibited a higher concentration when extracted using a dilution factor of 1:500.

TABLE 2

| Feces Sample | Consistency of Feces Matrix | Calprotectin Conc. [μg/g of the sample] 1:50 | 1:500 | EYR [%] |
|---|---|---|---|---|
| 3 | not assessed | 348 | 363 | 104 |
| 18 | not assessed | 376 | 457 | 122 |
| 20 | not assessed | 283 | 351 | 124 |
| 28 | not assessed | 326 | 411 | 126 |
| 29 | liquid | 2,621 | 3,436 | 131 |
| 40 | normal consistency | 1,333 | 3,579 | 268 |
| 41 | liquid | 427 | 472 | 111 |
| 42 | normal consistency | 1,069 | 2,285 | 214 |
| 43 | liquid | 2,310 | 6,000 | 260 |
| 44 | dry, hard | 1,177 | 6,000 | 510 |
| 45 | semi-liquid, not homogenous | 2,803 | 3,792 | 135 |
| 46 | normal consistency | 1,546 | 3,781 | 245 |
| 47 | normal consistency | 1,376 | 6,000 | 436 |
| 48 | normal consistency, not homogenous | 1,309 | 1,543 | 118 |
| 49 | normal consistency | 1,232 | 5,925 | 481 |
| 50 | normal consistency | 918 | 2,002 | 218 |
| 51 | normal consistency | 908 | 3,625 | 399 |
| 52 | normal consistency | 2,731 | 6,000 | 220 |
| 53 | not assessed | 2,207 | 4,403 | 200 |
| 54 | dry, hard | 663 | 1,518 | 229 |
| 55 | normal consistency | 597 | 821 | 137 |
| 56 | semi-liquid, not homogenous | 2,611 | 6,000 | 230 |
| 57 | normal consistency | 896 | 6,000 | 670 |
| 58 | not assessed | 1,362 | 5,548 | 407 |
| 59 | not assessed | 1,088 | 4,934 | 453 |
| 60 | not assessed | 2,776 | 6,000 | 216 |
| 61 | not assessed | 895 | 2,436 | 272 |
| 62 | not assessed | 598 | 931 | 156 |
| 63 | not assessed | 1,206 | 3,531 | 293 |
| | Min. | 283 | 351 | 104 |
| | Max. | 2,803 | 6,000 | 670 |
| | Avg. | 1,310 | 3,384 | 258 |

The extraction yield ratio (EYR) of a sample is given in % and is determined according to the following equation:

EYR=[(Concentration of the sample extracted using a dilution factor of 1:500)/(Concentration of the sample extracted using a dilution factor of 1:50)]*100%

The extraction yield ratio ranged from 104 to 670%. The average extraction yield ratio was 258%. These results were independent from the consistency of the feces sample as this effect can be reported from liquid (watery) to very hard samples. The difference between the extractive dilution at 1:500 vs. 1:50 was statistically highly significant showing a p value of <0.0001 (Wilcoxon Signed Rank test).

EXAMPLE 4: EFFECT OF STEPWISE EXTRACTIVE DILUTION FROM 1:50 UP TO 1:5,000 (COMPARATIVE EXAMPLE)

Interpreting the results of Example 3 it seems that the extraction capacity is limited at an extractive dilution of 1:50, particularly for feces samples containing a calprotectin concentration of more than approximately 500 µg/g of the sample. To test this hypothesis, the resulting homogenates of a 1:50 extraction were split immediately after the extracting step as described in Example 1a) into four aliquots. Three of these aliquots were diluted further 10-fold, 20-fold and 100-fold, respectively, with further extraction buffer (B-CAL-EX, BÜHLMANN Laboratories AG, Schoenenbuch, Switzerland) such that a final dilution of 1:500, 1:1,000 and 1:5,000, respectively, was obtained. The diluted homogenates were extracted further by vortexing for 1 minute at maximum speed. The diluted homogenates were allowed to sediment for at least 30 minutes. All homogenates were then assayed in the BÜHLMANN Calprotectin ELISA according to Example 2. Six feces samples with increasing calprotectin concentrations were tested and the results are shown in Table 3. It can be seen that calprotectin from feces containing high protein concentrations above 400 µg/g of the sample cannot be fully extracted out of the feces matrix at an extractive dilution of 1:50 and show a higher extraction yield when allowed to be re-extracted with 10- to 100-times higher volumes of extraction buffer.

But when comparing such a stepwise extraction using a first dilution of 1:50 and a second higher dilution of 1:500, 1:1,000, and 1:5,000, respectively (see Table 3) to an extraction using a direct dilution of 1:500, 1:1,000, and 1:5,000 in one step (see Example 5, Table 4), it can clearly be seen, that the calprotectin concentration is significantly higher with the inventive extraction using a direct dilution of 1:500, 1:1,000, and 1:5,000 in one step. A stepwise extraction is not sufficient to fully extract calprotectin from the feces samples.

TABLE 3

| Feces | Calprotectin Conc. [µg/g of the sample] after stepwise Extractive Dilutions with B-CAL-EX | | | |
|---|---|---|---|---|
| Sample | 1:50 | 1:500 | 1:1,000 | 1:5,000 |
| 64 | 310 | 367 | 341 | 407 |
| 65 | 1,006 | 1,200 | 1,137 | 1,170 |
| 66 | 1,867 | 3,728 | 4,073 | 3,958 |
| 67 | 1,915 | 1,992 | 2,899 | 1,601 |
| 68 | 2,700 | 6,098 | 6,707 | 4,880 |
| 69 | 3,291 | 6,215 | 6,345 | 5,605 |

EXAMPLE 5: EFFECT OF THE DILUTION FACTOR DURING THE EXTRACTION PROCESS ON CALPROTECTIN YIELD

Four feces samples were extracted according to Examples 1a) and 1b) by adding 50-, 100-, 250-, 500-, 1,000-, and 5,000-times the volume of extraction buffer (B-CAL-EX, BÜHLMANN Laboratories AG, Schoenenbuch, Switzerland) to the weighed-in feces. After 1 minute of vigorous vortexing each sample was allowed to sediment for approximately 30 minutes and then assayed in the BÜHLMANN Calprotectin ELISA as described in Example 2. From the results presented in Table 4 it can be seen that the higher the extractive dilution factor the higher is the mean extraction yield of calprotectin. Furthermore, it can be seen that in all tests the concentration of calprotectin was higher using a dilution in a range of 1:100 to 1:5,000 in comparison to a dilution of 1:50. An extraction using a dilution of 1:50 is not sufficient to fully extract calprotectin from the feces samples. The optimum extractive dilution factor is peaking around 1:250 to 1:1,000.

TABLE 4

| Feces | Calprotectin Conc. [µg/g of the sample] | | | | | |
|---|---|---|---|---|---|---|
| Sample | 1:50 | 1:100 | 1:250 | 1:500 | 1:1,000 | 1:5,000 |
| 65 | 918 | 1,163 | 1,543 | 2,433 | 1,435 | 1,822 |
| 66 | 1,647 | 2,398 | 4,075 | 7,182 | 7,524 | 6,746 |
| 70 | 2,042 | 3,361 | 2,725 | 3,651 | 3,867 | n.a. |
| 71 | 3,383 | 3,619 | 5,440 | 4,382 | 6,491 | n.a. |
| Mean | 1,608 | 2,128 | 2,807 | 3,629 | 4,063 | n.a. |

EXAMPLE 6: COMPARISON OF EXTRACTION BUFFERS

It can be learned from the state of the art literature that the constitution of the extraction buffer may significantly influence the extraction yield of calprotectin employing an extractive dilution from 1:2 up to 1:80 (U.S. Pat. No. 5,455,160; Tøn et al. (Clinica Chimica Acta 292 (2000) 41-54)). Hence, the influence of three different optimized, commercial extraction buffers was tested using an extractive dilution of 1:50 vs. 1:500 with each of them. Six feces samples were extracted using a dilution of 1:50 according to Example 1a) and 1:500 according to Example 1b), respectively, using the "BL" extraction buffer (B-CAL-EX; BÜHLMANN Laboratories AG, Schoenenbuch, Switzerland), the "ID" extraction buffer (EXBUF; Immundiagnostik AG, Bensheim, Germany) and the "CL" extraction buffer (FEC EXTR BUF 2,5x; Calpro AS, Lysaker, Norway). All resulting extracts were assayed in the BÜHLMANN Calprotectin ELISA as described in Example 2. The results are shown in Table 5. Although the absolute values of the measured calprotectin levels are somewhat variable for the three different extraction buffers, it could be shown for each of the three optimized extraction buffers that the extraction yield ratio was significantly higher (p<0.0001 by Wilcoxon test) when extracted by an extraction factor of 1:500 as compared to 1:50 (see also FIG. 3). The average increase in the extraction yield ratio (in a range of 234% to 249%) was remarkably similar between the three extraction buffers. This clearly shows that the higher extraction yield of calprotectin from extracted feces is almost exclusively dependent on the higher extractive dilution factor of 1:500. Noteworthy that the "CL" extraction buffer (FEC EXTR BUF 2,5x; Calpro AS, Lysaker, Norway) is the optimized buffer described in EP 0 937 259 B1, U.S. Pat. No. 5,455,160, and Ten et al. (Clinica Chimica Acta 292 (2000) 41-54) for which it has been stated that an extractive dilution factor of 1:50 and 1:80, respectively, is entirely sufficient for a full extraction of calprotectin from feces.

TABLE 5

| Feces | Extraction Buffer 1 ("BL") BÜHLMANN ELISA | | | Extraction Buffer 2 ("ID") BÜHLMANN ELISA | | | Extraction Buffer 3 ("CL") BÜHLMANN ELISA | | |
|---|---|---|---|---|---|---|---|---|---|
| | Calprotectin Conc. [μg/g of the sample] | | EYR | Calprotectin Conc. [μg/g of the sample] | | EYR | Calprotectin Conc. [μg/g of the sample] | | EYR |
| Sample | 1:50 | 1:500 | [%] | 1:50 | 1:500 | [%] | 1:50 | 1:500 | [%] |
| 72 | 79 | 102 | 129 | 41 | 87 | 212 | 67 | 95 | 142 |
| 73 | 411 | 454 | 110 | 216 | 278 | 129 | 335 | 562 | 168 |
| 74 | 633 | 791 | 125 | 456 | 786 | 172 | 773 | 1,526 | 197 |
| 75 | 1,245 | 5,459 | 438 | 856 | 3,599 | 420 | 1,839 | 5,716 | 311 |
| 76 | 1,553 | 4,515 | 291 | 824 | 2,356 | 286 | 1,477 | 4,013 | 272 |
| 77 | 1,688 | 5,399 | 320 | 999 | 2,723 | 273 | 1,932 | 6,125 | 317 |
| Mean | | | 236 | | | 249 | | | 234 |

TABLE 6

| Feces | Extraction Buffer 1 ("BL") CALPRO ELISA | | | Extraction Buffer 3 ("CL") CALPRO ELISA | | |
|---|---|---|---|---|---|---|
| | Calprotectin Conc. [μg/g of the sample] | | EYR | Calprotectin Conc. [μg/g of the sample] | | EYR |
| Sample | 1:50 | 1:500 | [%] | 1:50 | 1:500 | [%] |
| 72 | 53 | 60 | 113 | 64 | 84 | 131 |
| 73 | 258 | 319 | 124 | 274 | 413 | 151 |
| 74 | 509 | 538 | 106 | 494 | 1,021 | 207 |
| 75 | 1,004 | 3,357 | 334 | 982 | 3,733 | 380 |
| 76 | 1,030 | 2,187 | 212 | 925 | 2,722 | 294 |
| 77 | 1,738 | 3,041 | 175 | 2,166 | 3,956 | 183 |
| Mean | | | 177 | | | 224 |

EXAMPLE 7: COMPARISON/INFLUENCE OF CALPROTECTIN ELISA METHODS

It could be argued that the results generated in Example 6 are biased because all fecal extracts were measured in the same calprotectin assay, the BÜHLMANN Calprotectin ELISA, which is based on a sandwich assay technology using a set of two highly specific monoclonal antibodies. Hence the "BL" extracts and the "CL" extracts were also measured in an alternative ELISA assay, the Calprolabs™ Calprotectin ELISA (ALP) (Calpro AS, Lysaker, Norway) which is based on a sandwich assay technology using a monoclonal antibody for catching the calprotectin and polyclonal antibodies for detecting the bound calprotectin. Although the absolute values of the measured calprotectin concentrations are slightly different for the two extraction buffers, it could be shown also with the Calprolabs™ ELISA that the extraction yield was significantly higher (p=0.0024 by Wilcoxon test) when extracted using a dilution of 1:500 as compared to a dilution of 1:50 (Table 6). The average increase in extraction yield was 177% for the BÜHLMANN "BL" extraction buffer (B-CAL-EX; BÜHLMANN Laboratories AG, Schoenenbuch, Switzerland) and 224% for the Calpro "CL" extraction buffer (FEC EXTR BUF 2,5x; Calpro AS, Lysaker, Norway), respectively. Hence, the effect of a higher extraction yield of calprotectin from feces with an extractive dilution of 1:500 was independent from the ELISA assay used.

Figure 3:
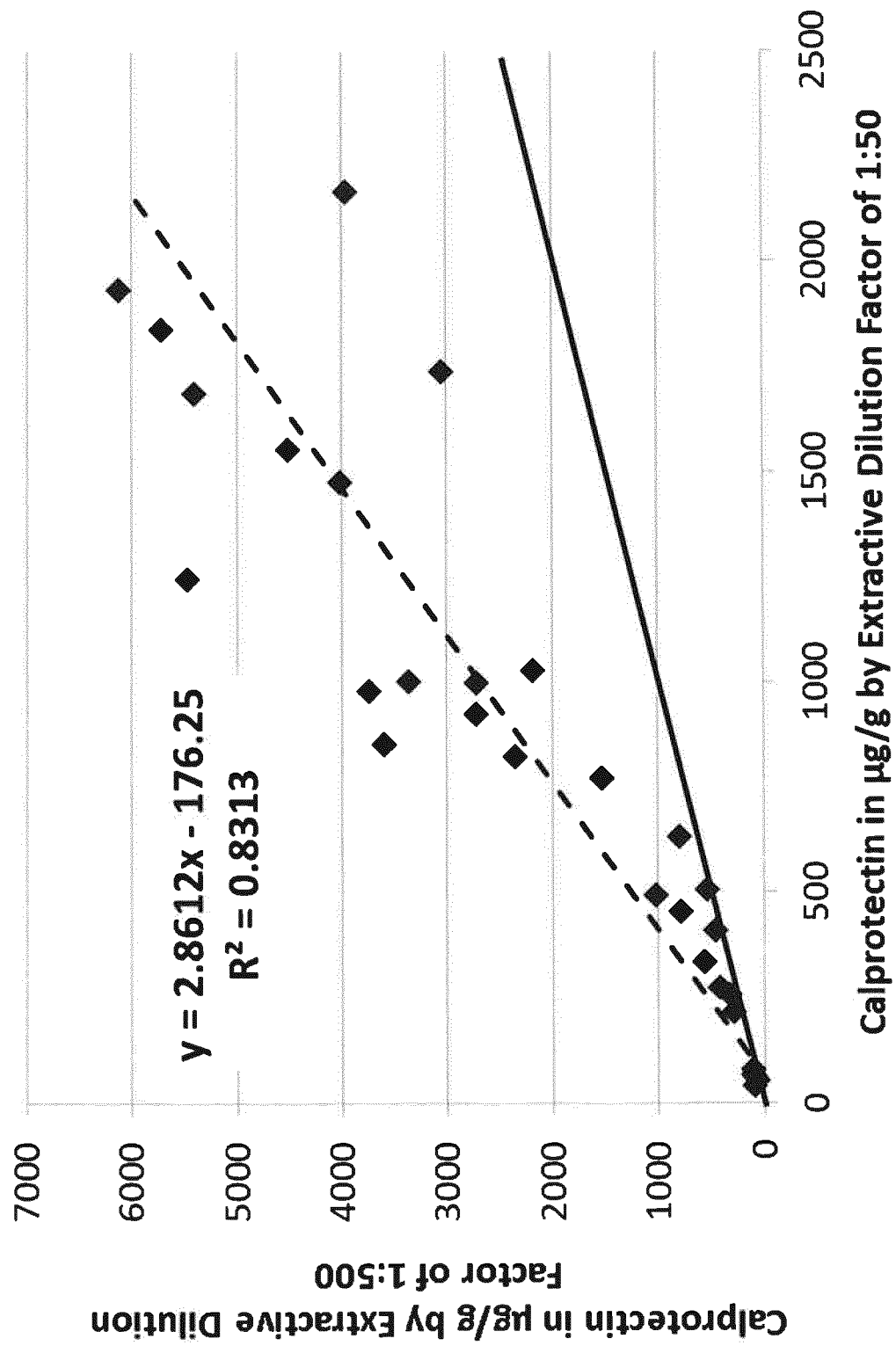

The results from Examples 6 and 7 are summarized by a regression analysis and presented in FIG. 3. From the slope of the regression line (dashed line) it can be read that the extraction yield of calprotectin is in average approximately 200% higher when the feces sample was extracted with a dilution of 1:500 as compared to 1:50. The graph also illustrates that almost any of the 1:500 feces extracts was reading above the identity line (solid, bold line) showing again the superior performance of the 1:500 extractive dilution.

EXAMPLE 8: CALEX™ DEVICES PROVIDING A DIRECT 1:500 EXTRACTION METHODOLOGY

In order to obtain an easy, proper, reliable and hygienic collection and extraction of feces with a direct extraction factor of 1:500, the CALEX™ Cap and CALEX™ Valve devices were developed (BÜHLMANN Laboratories AG, Schoenenbuch, Switzerland). These devices demand neither for a weighing-in step nor for any pipetting step prior to use of the final, homogenized fecal extract for the respective calprotectin assay, i.e. the BÜHLMANN Calprotectin ELISA (EK-CAL; BÜHLMANN Laboratories AG, Schoenenbuch, Switzerland).

Figure 4:
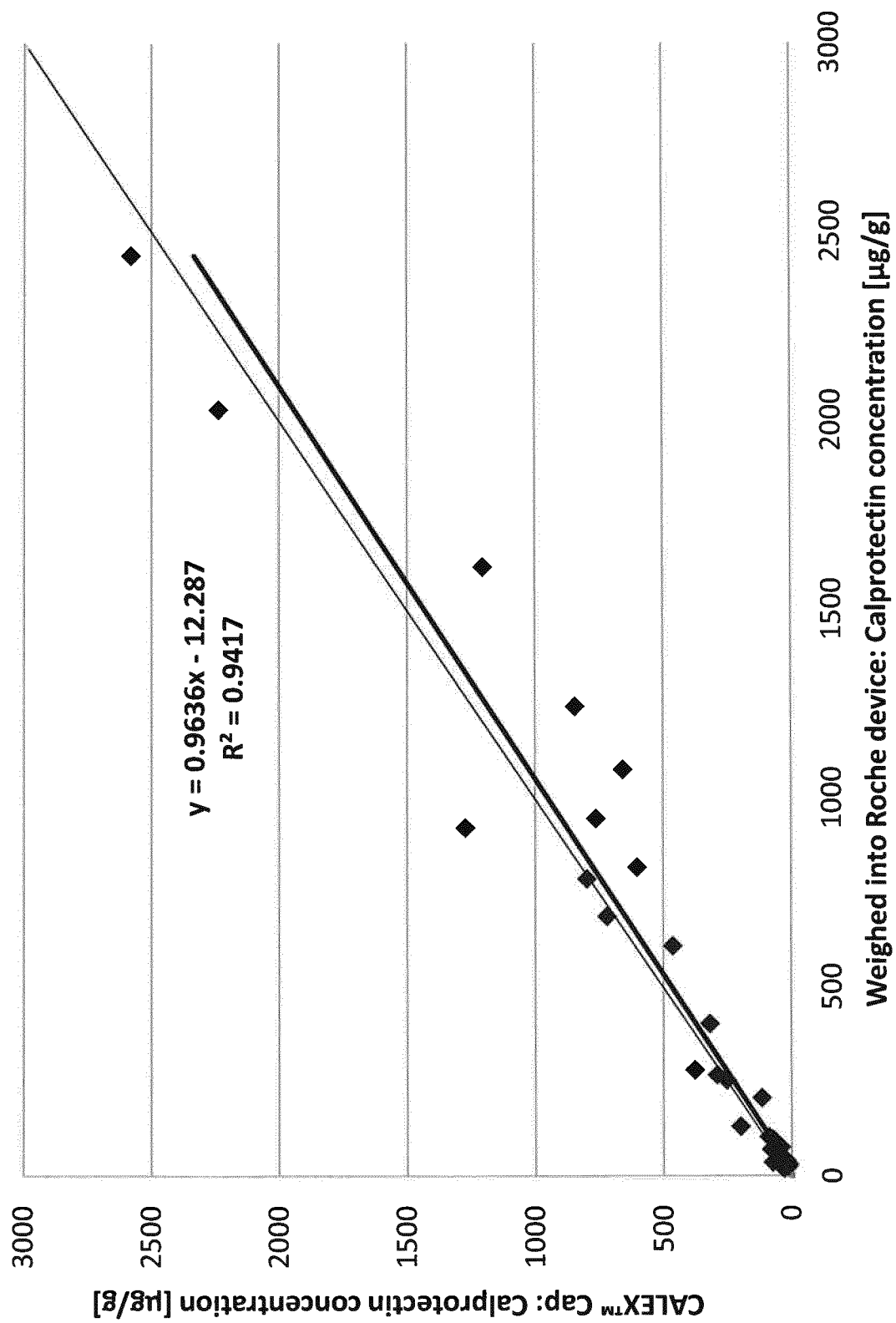

The performance of the CALEX™ Cap Device, described and used as illustrated in Example 1c), was compared to a quantitative "reference" weighing-in procedure using a fecal sample preparation kit (Cat.No. 10745804; Roche Diagnostics GmbH, Mannheim) according to Example 1b). The dosing tip of the sampling pin of the CALEX™ Cap device was introduced 5-times into a fecal sample at different locations to collect enough feces material within the grooves of the dosing tip. The sampling pin was then re-introduced into the extraction chamber of the CALEX™ Cap device through a funnel equipped with a transversal septum so that excess fecal material was stripped off the dosing tip of the sampling pin, and exactly 10±1 mg of fecal material was introduced into the extraction chamber filled with 5 ml of extraction buffer (B-CAL-EX; BÜHLMANN Laboratories AG, Schoenenbuch, Switzerland). The CALEX™ device was then vortexed at maximum speed for 30 seconds, left for 30 minutes and vortexed again for 30 seconds at maximum speed. The homogenized fecal extract was then allowed to sediment for 1 hour at ambient temperature (approximately 23° C.) and finally assayed in the BÜHLMANN Calprotectin ELISA. For the "reference" procedure, 8 to 12 mg of 40 different feces samples were weighed into the sample chamber of the base cap of the Roche device (Cat.No. 10745804; Roche Diagnostics GmbH, Mannheim). The body of the extraction tube was then pressed onto the filled base cap and 4 to 6 ml of extraction buffer (B-CAL-EX; BÜHLMANN Laboratories AG, Schoenenbuch, Switzerland) were added. The Roche tubes were then capped, vortexed for 1 minute at maximum speed, allowed to sediment for 1 hour at ambient temperature (approximately 23° C.) and finally assayed in the BÜHLMANN Calprotectin ELISA in the same run together with the 40 fecal extracts processed by the CALEX™ Cap devices. The comparison data are shown in FIG. 4. There was no significant difference between the two collection and extraction methods and devices, respectively, observed neither in accuracy (slope y=0.9636x) nor in precision/reliability ($R^2$=0.9417).

EXAMPLE 9: HANDLING AND PERFORMANCE OF LIQUID (WATERY) FECES

Liquid feces are very delicate to handle as they cannot be easily collected with the dosing tip of the CALEX™ devices (cf. Examples 1c) and 8) or of any other state of the art device using the same or similar sample collecting principles. This was also observed by Whitehead et al. (liquid sample 5 in FIG. 3 on page 58 of Ann. Clin. Biochem. 50 (2013) 53-61).

In this example we provide a very simple and reliable method to circumvent the problem of the inferior performance (particularly the greatly diminished extraction yield) of liquid (watery) feces samples. Exactly 10 µl of five watery feces samples were pipetted through the funnel into the extraction chamber of the CALEX™ Cap device pre-filled with 5 ml of extraction buffer (B-CAL-EX; BÜHLMANN Laboratories AG, Schoenenbuch, Switzerland) using a precision pipette leading to an extractive dilution of 1:500 (v/v). The CALEX™ device was then closed with the sampling pin and processed as described in Example 1c). Alternatively, a small portion (approximately 5 to 15 mg) of the five watery feces samples was transferred with a small spoon into a pre-weighed TPP plastic centrifuge tube (Techno Plastic Products AG, Trasadingen, Switzerland) and the net weight of the feces samples was determined with a precision balance. Then a 500-fold amount of extraction buffer (B-CAL-EX; BÜHLMANN Laboratories AG, Schoenenbuch, Switzerland) was added, the TTP tube tightly closed and the extraction was processed as described in Examples 1b) and 8 also leading to an extractive dilution of 1:500 (w/v). The calprotectin concentrations of the fecal extracts obtained by both methods were then measured in the BÜHLMANN Calprotectin ELISA. The calprotectin extraction yields and variability (CVs, coefficients of variation) of triplicate extractions for both methodological approaches were compared and are illustrated in Table 7.

It can be seen that for a semiliquid sample the "CALEX™ pipetting" method provides higher extraction yields, whereas for liquid samples the weighing-in method provides somewhat higher extraction yields.

However, both methods using a dilution of the sample in the buffered aqueous extraction medium of 1:500 (w/v or v/v) provide acceptable extraction yields, particularly when compared to other extraction tools which show much inferior extraction yields around 5% only, as reported in the state of the art literature (e.g. Whitehead et al., Ann. Clin. Biochem. 50 (2013) 53-61). The variability (CVs) between extractions of the same fecal sample is higher with the "CALEX™ pipetting" method, but still acceptable. This is due to the inhomogeneous nature of watery feces samples as they contain a lot of liquid, but also small solid portions. These small solid portions do contain much more of the calprotectin than the liquid portion. The liquid portion usually contains less than 10% of the total calprotectin of a watery fecal sample (data not shown). Therefore, it is very important, but sometimes not very easy, to mix the liquid (watery) fecal sample well before or while pipetting it.

TABLE 7

| Feces Sample | Consistency | Manual 1:50 | Replicate | Manual 1:500 | CALEX™ 1:500 | Statistics | Manual 1:500 | CALEX™ 1:500 | Recovery [%] |
|---|---|---|---|---|---|---|---|---|---|
| 78 | Semi-liquid | 142 | 1 | 152 | 188 | Mean Conc. | 155 | 171 | 110 |
| | | | 2 | 167 | 177 | SD | 11 | 21 | |
| | | | 3 | 146 | 147 | CV [%] | 7.1 | 12.6 | |
| 79 | Liquid | 93 | 1 | 93 | 88 | Mean Conc. | 93 | 56 | 60 |
| | | | 2 | 94 | 39 | SD | 1 | 27 | |
| | | | 3 | 94 | 43 | CV [%] | 0.8 | 48.4 | |
| 80 | Liquid | 21 | 1 | 29 | 26 | Mean Conc. | 27 | 27 | 99 |
| | | | 2 | 27 | 26 | SD | 1 | 2 | |
| | | | 3 | 27 | 29 | CV [%] | 4.9 | 5.7 | |
| 81 | Liquid | 1,267 | 1 | 2,883 | 2,256 | Mean Conc. | 2,568 | 2,047 | 80 |
| | | | 2 | 2,623 | 1,967 | SD | 345.8 | 182.7 | |
| | | | 3 | 2,198 | 1,918 | CV [%] | 13.5 | 8.9 | |
| 82 | Liquid | 52 | 1 | 69 | 52 | Mean Conc. | 63 | 43 | 68 |
| | | | 2 | 63 | 49 | SD | 6 | 14 | |
| | | | 3 | 56 | 27 | CV [%] | 10.1 | 31.8 | |
| | | | | | | Average (CV; Rec.) [%] | 7.3 | 21.5 | 83 |

EXAMPLE 10: STABILITY OF 1:50 VS. 1:500 EXTRACTS

In most cases fecal extracts are not immediately analyzed in the testing laboratory, being it because the sample has to be shipped from the patient's home or the doctor's office to the testing laboratory first or being it because the testing laboratory analyzes the fecal sample extracts batchwise, i.e. once a week. Hence, we have also tested the stability of the fecal extracts when refrigerated (at 2 to 8° C.) and at a temperature a few degrees above "room temperature", namely at 28° C. 39 feces samples were extracted 1:50 according to Example 1a) and 1:500 according to Example 1b) and then incubated for 1, 2, 3, and 6 days either at 2 to 8° C. or at 28° C. After the corresponding incubations the extracts were tested in the BÜHLMANN Calprotectin ELISA according to Example 2. Surprisingly, the inventors have found that the fecal extracts were much more stable, particularly at elevated temperature, when extracted and stored using an extractive dilution of 1:500 (i.e. using the CALEX™ devices from Examples 1c) and 8) as compared to an extractive dilution of 1:50 using a conventional state-of-the-art device. The summarized results in Tables 8a and 8b show that the fecal samples extracted with a dilution factor of 1:500 were perfectly stable at both temperatures for up to 6 days, whereas fecal samples extracted with a dilution factor of 1:50 show a gradual degradation over time. More detailed, the inventors have observed that a maximum of 3 and 4 fecal extracts were not entirely stable at 2 to 8° C. and 28° C., respectively, when extracted and stored at a dilution of 1:500 for up to 6 days (see Table 8a), whereas up to 16 and 23 fecal extracts were not stable at a temperature range of 2 to 8° C. and 28° C., respectively, when extracted and stored at a dilution of 1:50 for up to 6 days (see Table 8b). The criterion for "instability" in the context of this example is a recovery of calprotectin of less than 80% as compared to Time 0 (to).

After 24 hours up to 6 days the protein is degraded in average in a range of 2% to 13% when the extracted protein is kept at a temperature range of 2° C. to 8° C., and in a range of 6% to 26% when the extracted protein is kept at a temperature of 28° C., respectively, using an extractive dilution of 1:50 as applied in the state of the art. No degradation is visible at an extractive dilution of 1:500. The mean stability coefficient is in a range of 1.134 to 1.676 when calculated for the mean recoveries as compared to $t_0$.

TABLE 8a

| Feces Sample | Calprotectin Conc. [µg/g of the sample] Time 0 (Start) | Extractive Dilution by Factor 1:500 - Recovery [%]/Time 0 (Start) | | | | | | | |
|---|---|---|---|---|---|---|---|---|---|
| | | Storage Temperature 2-8° C. | | | | Storage Temperature 28° C. | | | |
| | | Day 1 | Day 2 | Day 3 | Day 6 | Day 1 | Day 2 | Day 3 | Day 6 |
| 9 | 25 | 104 | 106 | 106 | 106 | 92 | 87 | 94 | 79 |
| 16 | 30 | 105 | 111 | 115 | 111 | 111 | 105 | 98 | 91 |
| 13 | 36 | 111 | 122 | 121 | 125 | 125 | 122 | 119 | 114 |
| 6 | 38 | 104 | 113 | 115 | 124 | 132 | 137 | 126 | 126 |
| 15 | 38 | 108 | 118 | 115 | 115 | 121 | 113 | 73 | 100 |
| 12 | 47 | 102 | 109 | 106 | 113 | 119 | 111 | 115 | 111 |
| 1 | 59 | 119 | 126 | 129 | 141 | 145 | 143 | 147 | 139 |
| 27 | 60 | 85 | 69 | 77 | 75 | 97 | 50 | 50 | 42 |
| 2 | 64 | 108 | 118 | 121 | 132 | 136 | 144 | 144 | 147 |
| 21 | 69 | 141 | 99 | 106 | 109 | 117 | 104 | 107 | 109 |
| 14 | 70 | 108 | 112 | 118 | 124 | 136 | 132 | 134 | 129 |
| 31 | 77 | 155 | 117 | 122 | 130 | 112 | 124 | 129 | 129 |
| 8 | 78 | 97 | 110 | 124 | 123 | 160 | 136 | 132 | 132 |
| 25 | 78 | 160 | 108 | 101 | 121 | 126 | 121 | 126 | 122 |
| 7 | 109 | 106 | 111 | 112 | 116 | 115 | 110 | 109 | 109 |
| 24 | 123 | 169 | 111 | 115 | 122 | 119 | 129 | 124 | 147 |
| 4 | 167 | 102 | 105 | 59 | 63 | 129 | 139 | 69 | 71 |
| 11 | 196 | 113 | 107 | 120 | 117 | 123 | 112 | 123 | 137 |
| 5 | 230 | 110 | 112 | 110 | 118 | 112 | 107 | 110 | 116 |
| 10 | 237 | 105 | 108 | 111 | 121 | 116 | 122 | 120 | 132 |
| 22 | 249 | 160 | 106 | 110 | 107 | 129 | 118 | 120 | 133 |
| 20 | 351 | 112 | 101 | 119 | 109 | 138 | 101 | 108 | 92 |
| 3 | 363 | 116 | 119 | 59 | 66 | 137 | 138 | 71 | 75 |
| 28 | 411 | 128 | 98 | 105 | 114 | 106 | 126 | 127 | 137 |
| 18 | 457 | 93 | 90 | 93 | 98 | 106 | 86 | 92 | 91 |
| 30 | 623 | 139 | 113 | 115 | 129 | 122 | 131 | 133 | 127 |
| 39 | 756 | 206 | 126 | 146 | 179 | 127 | 210 | 195 | 217 |
| 26 | 781 | 136 | 112 | 118 | 128 | 122 | 130 | 144 | 154 |
| 23 | 790 | 135 | 126 | 131 | 134 | 124 | 124 | 126 | 115 |
| 17 | 853 | 105 | 105 | 109 | 111 | 114 | 107 | 119 | 118 |
| 32 | 1,125 | 180 | 115 | 128 | 142 | 113 | 125 | 128 | 196 |
| 34 | 1,448 | 140 | 107 | 148 | 117 | 147 | 129 | 138 | 134 |
| 19 | 2,428 | 118 | 108 | 115 | 124 | 120 | 105 | 114 | 122 |
| 37 | 2,462 | 135 | 117 | 128 | 144 | 106 | 116 | 122 | 113 |
| 38 | 3,053 | 158 | 101 | 104 | 103 | 99 | 106 | 122 | 141 |
| 29 | 3,244 | 127 | 110 | 103 | 111 | 99 | 116 | 123 | 128 |
| 36 | 4,190 | 84 | 91 | 93 | 95 | 59 | 106 | 104 | 218 |
| 33 | 4,857 | 109 | 135 | 119 | 122 | 93 | 133 | 128 | 134 |
| 35 | 4,961 | 108 | 122 | 132 | — | 94 | 131 | 148 | — |
| Mean | as compared to Time 0 | 123 | 110 | 112 | 117 | 118 | 120 | 118 | 124 |
| Mean | as compared to Day 1 | 100 | 89 | 91 | 95 | 100 | 102 | 100 | 106 |

| | Storage 2-8° C. | | | | Storage 28° C. | | | |
|---|---|---|---|---|---|---|---|---|
| | Day 1 | Day 2 | Day 3 | Day 6 | Day 1 | Day 2 | Day 3 | Day 6 |
| Number of Samples analyzed | 39 | 39 | 39 | 38 | 39 | 39 | 39 | 38 |
| Feces Extracts showing <80% Recovery as compared to Time 0 | 0 | 1 | 3 | 3 | 1 | 1 | 4 | 4 |

TABLE 8b

| | Calprotectin Conc. [μg/g of the sample] | Extractive Dilution by Factor 1:50 - Recovery [%]/Time 0 (Start) | | | | | | | |
|---|---|---|---|---|---|---|---|---|---|
| Feces | Time 0 | Storage Temperature 2-8° C. | | | | Storage Temperature 28° C. | | | |
| Sample | (Start) | Day 1 | Day 2 | Day 3 | Day 6 | Day 1 | Day 2 | Day 3 | Day 6 |
| 9 | 18 | 96 | 118 | 108 | 116 | 108 | 110 | 101 | 95 |
| 16 | 3 | 103 | 115 | 104 | 114 | 97 | 118 | 104 | 100 |
| 13 | 43 | 119 | 132 | 57 | 64 | 121 | 122 | 54 | 50 |
| 6 | 39 | 80 | 122 | 59 | 62 | 114 | 129 | 58 | 58 |
| 15 | 36 | 112 | 113 | 98 | 111 | 99 | 94 | 89 | 102 |
| 12 | 43 | 96 | 105 | 95 | 97 | 93 | 103 | 90 | 85 |
| 1 | 90 | 98 | 98 | 91 | 93 | 92 | 91 | 74 | 76 |
| 27 | 51 | 107 | 116 | 108 | 116 | 104 | 107 | 99 | 99 |
| 2 | 59 | 100 | 91 | 86 | 80 | 65 | 45 | 57 | 40 |
| 21 | 71 | 102 | 104 | 104 | 114 | 98 | 108 | 101 | 101 |
| 14 | 64 | 103 | 106 | 91 | 110 | 100 | 96 | 99 | 97 |
| 31 | 65 | 93 | 100 | 100 | 93 | 91 | 107 | 105 | 93 |
| 8 | 73 | 72 | 77 | 69 | 72 | 61 | 65 | 61 | 51 |
| 25 | 80 | 97 | 107 | 107 | 111 | 119 | 102 | 94 | 78 |
| 7 | 127 | 106 | 112 | 101 | 89 | 89 | 89 | 123 | 67 |
| 24 | 163 | 185 | — | 176 | 88 | 185 | — | 118 | 59 |
| 4 | 125 | 95 | 94 | — | 73 | 81 | 76 | 73 | 70 |
| 11 | 175 | 99 | 95 | 86 | 75 | 78 | 67 | 58 | 53 |
| 5 | 238 | 91 | 64 | 69 | 61 | 70 | 67 | 63 | 45 |
| 10 | 213 | 106 | 85 | 77 | 89 | 98 | 84 | 79 | 67 |
| 22 | 253 | 97 | 91 | 96 | 98 | 92 | 82 | 77 | 62 |
| 20 | 283 | 95 | 82 | 86 | 79 | 94 | 82 | 86 | 79 |
| 3 | 348 | 81 | 97 | 101 | 98 | 91 | 81 | 72 | 63 |
| 28 | 326 | 124 | 115 | 102 | 94 | 100 | 105 | 106 | 80 |
| 18 | 376 | 103 | 116 | 92 | 94 | 99 | 98 | 101 | 85 |
| 30 | 565 | 84 | 88 | 86 | 81 | 119 | 89 | 95 | 90 |
| 39 | 731 | 63 | 96 | 87 | 73 | 85 | 48 | 37 | 28 |
| 26 | 711 | 112 | 85 | 89 | 77 | 94 | 80 | 76 | 74 |
| 23 | 886 | 84 | 73 | 61 | 58 | 56 | 76 | 59 | 62 |
| 17 | 795 | 64 | 80 | — | 72 | 88 | 67 | 72 | 56 |
| 32 | 1,028 | 125 | 116 | 121 | 115 | 120 | 131 | 112 | 88 |
| 34 | 1,696 | 95 | 81 | 80 | 82 | 79 | 84 | 96 | 93 |
| 19 | 2,329 | 64 | 87 | 79 | 71 | 68 | 71 | 76 | 56 |
| 37 | 1,776 | 65 | 70 | 68 | 50 | 60 | 61 | 64 | 50 |
| 38 | 1,704 | 121 | 131 | 139 | 115 | 118 | 137 | 140 | 128 |
| 29 | 2,409 | 71 | 50 | 54 | 40 | 52 | 46 | 50 | 37 |
| 36 | 4,319 | 86 | 93 | 96 | 90 | 111 | 71 | 66 | 58 |
| 33 | 2,739 | 72 | 66 | 69 | 64 | 49 | 68 | 62 | 63 |
| 35 | 1,417 | 140 | 115 | 113 | 127 | 120 | 123 | 125 | 132 |
| Mean | as compared to Time 0 | 98 | 97 | 92 | 87 | 94 | 89 | 84 | 74 |
| Mean | as compared to Day 1 | 100 | 99 | 94 | 89 | 100 | 95 | 89 | 78 |

| | Storage 2-8° C. | | | | Storage 28° C. | | | |
|---|---|---|---|---|---|---|---|---|
| | Day 1 | Day 2 | Day 3 | Day 6 | Day 1 | Day 2 | Day 3 | Day 6 |
| Number of Samples analyzed | 39 | 38 | 37 | 39 | 39 | 38 | 39 | 39 |
| Feces Extracts showing <80% Recovery as compared to Time 0 | 8 | 6 | 11 | 16 | 10 | 13 | 20 | 23 |

The present invention provides a simple, sensitive and specific determination tool of proteins in GI tract samples. The determination of proteins, e.g. calprotectin, elastases or hemoglobin, in GI tract samples leads to more accurate and reproducible results than with state of the art methods. The measured concentrations, particularly in GI tract samples containing high levels of the protein, are significantly higher. Therefore the protein determination yields more accurate levels which are particularly important during therapy follow-up of affected patients with inflammations of the gastrointestinal tract. The present invention also leads to more stable protein extracts which simplifies sample collection by and transportation from the affected patient to the doctor's or testing laboratory in terms of efficacy, storage conditions (no cooling chain needed) and shipping time (no express services needed).

The invention claimed is:
1. A method for determining the concentration of a calprotectin protein in a gastrointestinal (GI) tract sample taken from a human or an animal, comprising the steps of
   a) Collecting a watery GI tract sample or a non-watery GI tract sample;
   b) Mixing the sample of step a) with a determined amount of buffered aqueous extraction medium to extract cal- protectin from the sample wherein a dilution of the sample in the buffered aqueous extraction medium in a range of 1:450 to 1:1000 w/vol is obtained for the non-watery GI tract sample and wherein a dilution of the sample in the buffered aqueous extraction medium in a range of 1:450 to 1:1000 is obtained for the watery GI tract sample;

c) Homogenizing the mixture of step b) to extract calprotectin from the sample; and d) Performing an immunoassay by using the mixture obtained in step c) to determine the concentration of the calprotectin protein.

2. The method according to claim 1, wherein the protein is present in the GI tract sample in a concentration range of 1 ng/ml of the sample to 100 mg/ml of the sample in case of a watery GI tract sample or in a concentration range of 1 ng/g of the sample to 100 mg/g of the sample in case of a non-watery GI tract sample.

3. The method according to claim 1, wherein the stability coefficient of the protein is in a range of 1.001 to 15.

4. The method according to claim 1, wherein the protein in the buffered aqueous extraction medium is stable at a temperature range of 2 to 42° C. for a time period of 1 to 28 days.

5. The method according to claim 1, wherein the protein concentration in the sample is higher than 300 µg/g of the sample in case of a non-watery GI tract sample and 300 µg/ml of the sample in case of a watery GI tract sample.

6. The method according to claim 1, wherein the GI tract sample is feces.

7. The method according to claim 1, wherein in step b) a dilution in a range of 1:450 to 1:550 is obtained.

8. The method according to claim 1, wherein the animal is a dog, cat, monkey, bovine, pig, horse, rat or mouse.

9. The method according to claim 1, wherein in step a) 1 to 1,000 mg of the sample are collected.

10. The method according to claim 9, wherein in step a) 2 to 100 mg of the sample are collected.

11. The method according to claim 1, wherein the immunoassay in step d) is selected from the group comprising an enzyme-linked immunosorbent assay (ELISA), an immunoturbidimetric assay, an immunochromato-graphic assay and a flow-assisted cytometric assay.

12. The method according to claim 1, wherein the determination in step d) is carried out visually or further by a method selected from the group comprising reflectometry, absorbance, fluorescence, chemiluminescence, electrochemiluminescence, UV/VIS spectroscopy, amperometry, magnetometry, voltametry, potentiometry, conductometry, coulometry, polarography, and electrogravimetry.

13. The method according to claim 2, wherein the stability coefficient of the protein is in a range of 1.001 to 15.

14. The method according to claim 13, wherein in step b) a dilution in a range of 1:450 to 1:550 is obtained.

15. The method according to claim 2, wherein the protein concentration in the sample is higher than 300 µg/g of the sample in case of a non-watery GI tract sample and 300 µg/ml of the sample in case of a watery GI tract sample.

16. The method according to claim 13, wherein the protein concentration in the sample is higher than 300 µg/g of the sample in case of a non-watery GI tract sample and 300 µg/ml of the sample in case of a watery GI tract sample.

17. The method according to claim 14, wherein the protein concentration in the sample is higher than 300 µg/g of the sample in case of a non-watery GI tract sample and 300 µg/ml of the sample in case of a watery GI tract sample.

* * * * *